United States Patent [19]

Aubert

[11] Patent Number: 5,393,913
[45] Date of Patent: Feb. 28, 1995

[54] N-FORMYLANILINES

[75] Inventor: Thierry Aubert, St. Genis Laval, France

[73] Assignee: Rhone-Poulenc Inc., Research Triangle Park, N.C.

[21] Appl. No.: 25,503

[22] Filed: Mar. 3, 1993

[51] Int. Cl.$^6$ .................. C07C 255/02; C07C 327/06; C07D 233/04
[52] U.S. Cl. ..................................... 558/394; 564/74; 564/77; 564/218; 548/324.1; 548/325.1
[58] Field of Search .......................... 548/325.1, 324.1; 564/218, 74, 77; 558/394

[56] References Cited

U.S. PATENT DOCUMENTS

| | | | |
|---|---|---|---|
| 2,809,984 | 10/1957 | Buc | 558/394 |
| 3,108,038 | 10/1963 | Fielding et al. | 564/218 X |
| 3,488,423 | 1/1970 | Doebbl et al. | 548/324.1 X |
| 3,829,454 | 8/1974 | Schladetsch | 558/394 |
| 3,915,980 | 10/1975 | Gebert et al. | 548/324.1 |
| 3,965,139 | 6/1976 | Scozzie | 558/394 |
| 3,966,789 | 6/1976 | Oishie et al. | 558/394 |
| 4,460,603 | 7/1984 | Chan | 424/324 |
| 4,743,613 | 5/1988 | Frazee et al. | 514/398 |
| 4,898,878 | 2/1990 | Shapiro et al. | 514/386 |

FOREIGN PATENT DOCUMENTS

| | | | |
|---|---|---|---|
| 0396427 | 11/1990 | European Pat. Off. | 548/325.1 |
| 0427445 | 5/1991 | European Pat. Off. | 564/74 |
| 0437640 | 7/1991 | European Pat. Off. | 564/74 |

*Primary Examiner*—Floyd D. Higel
*Attorney, Agent, or Firm*—James G. Passé

[57] ABSTRACT

The present invention relates to N-carbonyl anilines which are intermediates for the preparation of pesticidal 1-aryl imidazoles and to processes for making them.

1 Claim, No Drawings

N-FORMYLANILINES

BACKGROUND OF THE INVENTION

1. Field of the Invention

The present invention relates to novel N-carbonyl anilines which are further N-substituted by means of a radical cyano methylene or carbothioamide methylene. These compounds are useful and valuable intermediates for the preparation of 1-aryl imidazoles which are known, by U.S. Ser. No. 07/606518 filed on Oct.31, 1990,now U.S. Pat. No. 5,223,525, as pesticides for controlling arthropod, nematode, helminth or protozoan pests and more particularly for controlling arthropods, especially mites or foliar or soil insects, without causing injury to crop plants. The invention relates also to the process of preparation of such 1-aryl imidazoles from the intermediates hereabove defined.

2. Discussion of the Related Art

Various substituted N-carbonyl anilines are known to be useful as intermediates of biologically active material.

U.S. Pat. Nos. 3200151 and 3131218 describe N-cyanomethyl N-formyl 2,6-dimethylaniline as intermediates of pharmaceuticals.

SUMMARY OF THE INVENTION

An objective of the present invention is to provide a new process to achieve the preparation of N-carbonyl anilines which are further N-substituted by means of a radical cyano methylene or carbothioamide methylene.

A further objective of the present invention is to provide a new process to achieve the preparation of pesticidal 1-aryl imidazoles.

These and other objectives of the invention shall become readily apparent from the detailed description of the present invention.

Therefore the present invention provides novel N-carbonyl anilines (including their stereoisomers, resulting from an either optical or geometrical isomery) of the general formula I:

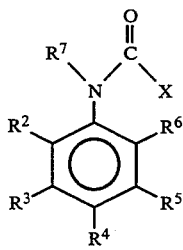
(I)

wherein:

X is a hydrogen atom or a $C_1$ to $C_4$ straight chain or branched chain alkyl group, which group is unsubstituted or substituted by one or more halogen atoms which are the same or different, up to full substitution of the alkyl moiety; and $R^2$, $R^3$, $R^4$, $R^5$, $R^6$ represent a hydrogen or a halogen atom or a $C_1$ to $C_4$ straight chain or branched chain alkyl group, which group is unsubstituted or substituted by one or more halogen atoms which are the same or different, up to full substitution of the alkyl moiety; and $R^7$ represents a group —CHY—CN or —CHY—CS—$NH_2$, in which Y is a hydrogen atom or a $C_1$ to $C_4$ straight chain or branched chain alkyl group provided that $R^2$ and $R^6$ are not simultaneously a methyl when X and $R^7$ represent, respectively, a hydrogen atom and a $CH_2$—CN group.

The formula I wherein $R^7$ represents a group —CHY—CN is hereafter designated with the symbol 3. The formula I wherein $R^7$ represents a group —CHY—CS—$NH_2$ is hereafter designated with the symbol 4.

According to a preferred feature of the invention, the novel N-carbonyl anilines are selected from amongst the compounds of the general formula II:

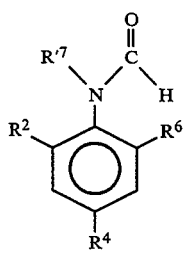
(II)

wherein:

$R^2$, $R^4$, $R^6$ represent a hydrogen or a halogen atom or a $C_1$ to $C_4$ straight chain or branched chain alkyl group, which group is unsubstituted or substituted by one or more halogen atoms which are the same or different, up to full substitution of the alkyl moiety;

$R'^7$ represents a group —$CH_2$—CN or —$CH_2$—CS—$NH_2$; provided that $R^2$ and $R^6$ are not simultaneously a methyl when $R'^7$ represents a $CH_2$—CN group.

According to a further preferred feature of the invention, the novel N-carbonyl anilines are selected from amongst the compounds of formula II wherein:

$R^2$ and $R^6$ are a halogen or a hydrogen, and $R^4$ is a halogen.

The novel N-carbonyl anilines of the present invention are useful for the preparation of 1-aryl imidazoles which are known to exhibit pesticidal properties, especially as insecticides or miticides or both, such as the following compounds of formula III:

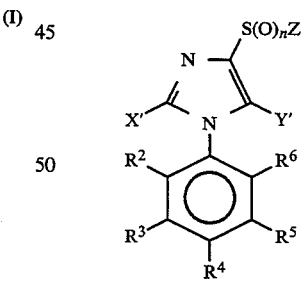
(III)

wherein:

$R^2$, $R^3$, $R^4$, $R^5$, $R^6$, X', Y' represent a hydrogen or a halogen atom or a $C_1$ to $C_4$ straight chain or branched chain alkyl group, which group is unsubstituted or substituted by one or more halogen atoms which are the same or different, up to full substitution of the alkyl moiety; and n is 0, 1, or 2; and Z represents a $C_1$ to $C_4$ straight chain or branched chain alkyl group, which group is unsubstituted or substituted by one or more halogen atoms which are the same or different, up to full substitution of the alkyl moiety.

DESCRIPTION OF THE PREFERRED EMBODIMENTS

Methods or Processes of Synthesis

The general manufacturing process of the novel N-carbonyl anilines of formula I, namely 3 and 4, is described in the Scheme I below, in which the substituents of the various compounds are those defined in the general formula (I).

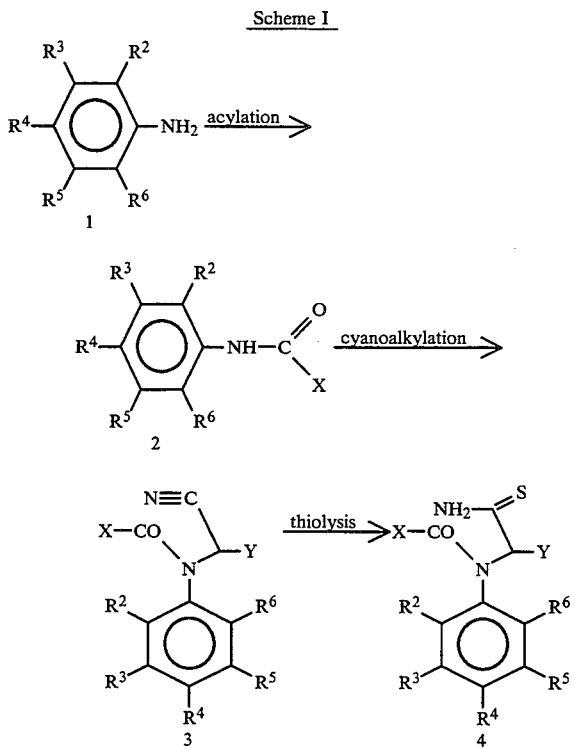

In Scheme I the starting materials, the uncarbonylated anilines 1, are generally commercially available or may be prepared following well known literature procedures. Well known procedures may be found by the man skilled in the art in general Chemistry Handbooks as well as in the literature identified in the Chemical Abstracts.

In a first step, the manufacturing process of the N-carbonylated anilines of formula 2, starting from the compounds of formula 1, is described hereafter.

When X represents a $C_1$ to $C_4$ straight chain or branched chain alkyl group, which group is unsubstituted or substituted by one or more halogen atoms which are the same or different, up to full substitution of the alkyl moiety, the N-carbonylated anilines 2 may be prepared by reacting in a liquid medium a substituted aniline of the general formula 1 with anhydrides of lower alkanoic acids of formula (5):

$$(X-CO)_2O \qquad (5)$$

The specific anhydride is chosen according to the exact formula of the anilines which is sought.

When X represents a hydrogen, the N-carbonylated anilines 2 may be prepared by reacting a substituted aniline of the general formula 1 with the anhydride of formula:

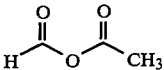

according to the methods described in Tet. Lett. 1982, 23, 3315 and J. Org. Chem. 1958, 23, 727 or similar methods adapted by the man skilled in the art choosing adequately the substituents.

In a second step, the manufacturing process of the compounds of formula 3, starting from the compounds of formula 2, is described.

The cyano derivatives of N-carbonylated anilines, of formula 3 in the Scheme I in which X, Y, and $R^2$ to $R^6$ are as defined in general formula I, are novel compounds, provided that $R^2$ and $R^6$ are not simultaneously a methyl when X and Y both represent a hydrogen atom. They may be prepared from the corresponding N-carbonylated anilines, of formula 2, by cyanoalkylation, that is to say by reacting a compound of formula (6):

$$\Sigma-CHY-CN \qquad (6)$$

wherein:

$\Sigma$ is a halogen, hydroxyde, alkylcarbonyloxy, haloalkylcarbonyloxy, arylcarbonyloxy, alkylsulfonyloxy, haloalkylsulfonyloxy, arylsulfonyloxy, preferably phenylsulfonyloxy;

Y has the same definition as in formula I.

This reaction is carried out in a biphasic reaction medium in conditions known as liquid-liquid phase transfer conditions. This means that there is an organic liquid phase and an aqueous liquid phase with transfer of reactants and/or catalyst from one phase to the other.

Some of the compounds of formula 6 are commercial, others can be prepared by methods known by the man skilled in the art.

When $\Sigma$ is a phenylsulfonyloxy, the preparation of the compound of formula 6 may be done according to the method described in Acta Pol. Pharm. 23 (5), p. 417 (1966). In this case, the compound of formula 6 may be implemented in the cyanoalkylation reaction without being isolated or purified: the aqueous phase in which this compound is obtained can be used as the aqueous liquid phase of the cyanoalkylation reaction.

The organic phase for the cyanoalkylation reaction is mainly an organic solvent wherein the anilines are soluble. Advantageously, this solvent may be an aliphatic or aromatic hydrocarbon which may be halogenated, or a derivative of such compounds having an oxygen atom therein which forms an ether bond. Preferred organic solvents are chlorinated hydrocarbons such as dichloromethane, or aromatic hydrocarbons such as toluen or monochlorobenzene.

The aqueous liquid phase comprises a water soluble base and a phase transfer catalyst. The water soluble base may be organic or inorganic, and is preferably an hydroxide or carbonate of alkaline or earth-alkaline metal. The liquid-liquid phase transfer catalysts are well known; alkylammonium halides are preferred. The ratio: catalyst/starting material 2 (defined as mole number/mole number), is generally between 0.02 and 0.4, preferably between 0.05 and 0.25. The reaction temperature is generally between −10° and 50° C., preferably between 5° and 20° C. (room temperature).

In a third step, the manufacturing process of the compounds of formula 4, starting from the compounds of formula 3, is now described.

The carbothioamide methylene substituted N-carbonylated aniline, of formula 4 in the Scheme I in which X, Y and $R_2$ to $R_6$ are as defined in general formula I, are novel compounds which may be prepared by thiolysis of the cyano derivatives of N-carbonylated anilines of formula 3 in the Scheme I. This reaction of thiolysis is a reaction known per se, and any procedure known to thiolyze a nitrile group into an amino thiocarbonyl group may be used, such as:

* action of esters of the dithiophosphoric acid as described in J. Heterocyclic Chem. 28, 1607 (1991); or
* action of phosphorus polysulfide, preferably decasulfide, in presence of an alkaline sulfide, as described in Synth. Commun., 22 (10), 1397 (1992).

The preferred procedure for thiolysis involves a base-catalyzed action of hydrogen sulfide (gas) under either gas-liquid or gas-liquid-liquid phase transfer conditions. The reaction may be carded out under an hydrogen sulfide pressure comprised in the range from 1 to 4 bar, preferably from 1 to 2 bar. The ratio: mole number of hydrogen sulfide/mole number of cyano derivatives 3, is generally in the range from 1 to 10, preferably from 1 to 2. The reaction temperature is generally in the range from 25° to 80° C., preferably from 30° to 40° C.

In the case of a gas-liquid system, the liquid phase may be a polar organic solvent wherein the cyano derivatives 3 are soluble. Advantageously, the solvent may be a protic solvent such as an alcohol or an aprotic solvent such as dimethylformamid, dimethylsulfoxid, sulfolane, acetone, or pyridine. The catalytic base may be an amine (as described in J. Chem. Eng. Data, 13, 130 (1968)), an hydroxide or alkoxide of alkaline or earth-alkaline metal, a basic ion-exchange resin, an alkylammonium hydroxide, an hydrosulphide of alkaline metal, or sodium sulphide. Preferred bases are aromatic amines such as pyridin or dimethylaminopyridin, primary, secondary or tertiary aliphatic amines including alkanolamines, such as ethanolamine and diethanolamine, tetra-(lower alkyl) guanidines, ammonia, or a mixture of amines such as a mixture thereof, preferably triethylamine and pyfidine. The ratio: concentration of catalytic base/concentration of cyano derivatives 3(defined as mole number/mole number ) is generally between 0 and 3, preferably between 0.8 and 1.5.

In the case of a gas-liquid-liquid system, such as described in Synthesis, 917 (1978), one liquid phase is an organic one which is mainly an aliphatic or aromatic hydrocarbon, which may be halogenated, or an ether. Preferred organic solvents are chlorinated aromatic hydrocarbon, such as dichlorobenzene, or an ether such as diphenyl ether. The other liquid phase is an aqueous liquid phase which comprises a phase transfer catalyst and sodium sulphide. Preferred phase transfer catalyst are tetra-alkylammonium halides and the ratio: mole number of catalyst/mole number of starting material 3 is generally between 0.01 and 0.1. The ratio: mole number of sodium sulphide/mole number of starting material 3 is generally between 0.02 and 0.2.

Scheme II herebelow now describes, starting from the novel compounds according to the invention, of formula I, namely of formula 4, the general manufacturing process of some of the 1-aryl imidazoles of formula III, namely the 1-aryl imidazoles of formula 10, wherein the definitions of X, Y, $R_2$, $R_3$, $R_4$, $R_5$, $R_6$ are those given in the general formula I, and $R_7$ and $R_8$ represent F, Cl, Br or a perfluoroalkyl group.

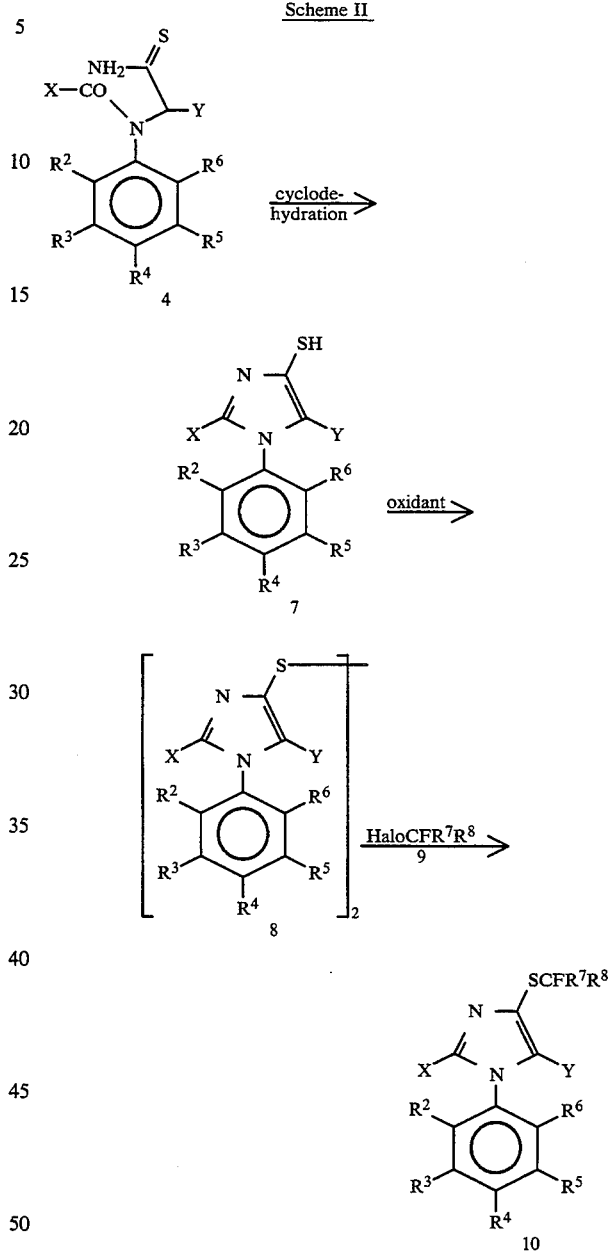

Scheme II

In a first step, we describe hereafter the manufacturing process of an intermediate thiol of formula 7 starting from the novel compounds of the present invention, of formula 4.

Cyclodehydration of carbothioamide methylene substituted N carbonylated amines of formula 4 is generally known in the art (J. Org. Chem. 1987, 52, 2977 and J. Org. Chem. 1989, 54, 4570), and any method similar to the described methods can be used, preferably heating in formic acid.

In a second step, the manufacturing process of a compound of formula 8, starting from an intermediate thiol of formula 7, is described.

The intermediate thiol 7 may either be oxidized in situ, without isolation, to the corresponding disulfide of the general formula 8, by the oxygen present in the solvent used for its preparation, for example by the oxygen present in the formic acid if the formic acid itself is used as solvent, or isolated as crude material and oxidized by further treatment with an oxidizing agent. The oxidizing agent may be oxygen or a hydrogen peroxyde, and then the reaction is conducted in a suitable inert solvent, such as acetonitrile, water, a mixture of both. If the oxidizing agent is a sulfoxide, such as dimethylsulfoxide or tetramethylene sulfoxide, then the sulfoxide itself is also used as solvent for the reaction. The oxidizing agent may also be bromine. Such a reaction is conveniently carried out at a reaction temperature from about 0° to about 200° C., preferably at a temperature from about 20° to about 150° C. Representative procedures are reported in J. March, "Advanced Organic Chemistry", Third Ed., 1985, Wiley-Interscience, p. 1092 and in references therein, in O. G. Lowe, J. Org. Chem., 1975, 40, 2096, and in T. J. Wallace, J. Am. Chem. Soc., 1964, 86, 2018.

A sulfide 10 may be prepared by the reaction of the disulfide intermediate 8 and a perhaloalkane compound of the formula 9, HaloCFR$_7$R$_8$, wherein Halo is a halogen, preferably Cl, Br or I, R$_7$ is F, Cl or Br, and R$_8$ is F, Cl, Br or a perfluoroalkyl group, with a reducing agent which can promote the formation of the free radical CFR$_7$R$_8$ (from HaloCFR$_7$R$_8$). The reducing agent is preferably chosen from a metal consisting of zinc, aluminum, cadmium, manganese or a compound with an oxide of sulfur, e.g. a dithionite or a hydroxymethylsulfinate. The alkaline dithionite, alkaline earth or the metal dithionite corresponds to the formula M$_n$(S$_2$O$_4$), in which n can be 1 or 2 depending upon the valence of the metal M. When a dithionite or a hydroxymethylsulfinate is used, a base is needed. The base can be chosen from among an alkaline hydroxide, alkali earth hydroxide, ammonia, alkylamine, triethylbenzylammonium or the salt of weak acids such as disodium phosphate, sodium metabisulfite, sodium hydrogen sulfite, sodium borate. The solvents used for the reaction are those which can solubilize the dithionite or the hydroxymethylsulfinate, and the compounds 8 and 9. Useful solvents are acetonitrile, dimethylformamide, formamide, dimethylacetamide, hexamethylphosphoramide, N-methylpyrrolidone, dimethylsulfoxide or sulfolane. The reaction temperature is from about 10° C. to about 200° C., preferably from about 50° C. to about 150° C. Typical procedures are similar to those reported by C. Wakselman et al., J. Chem. Soc., Chem. Commun., 1991, 993 and in references therein.

The sulfides of the general formula 10, in which Y is a hydrogen atom and the other groups are as defined above, are also useful intermediates in the preparation of compounds of the general formula III, in which Y' is a halogen atom, Z is CFR$_7$R$_8$, n is 0, and the other groups are as defined above. The reaction is represented by the following equation:

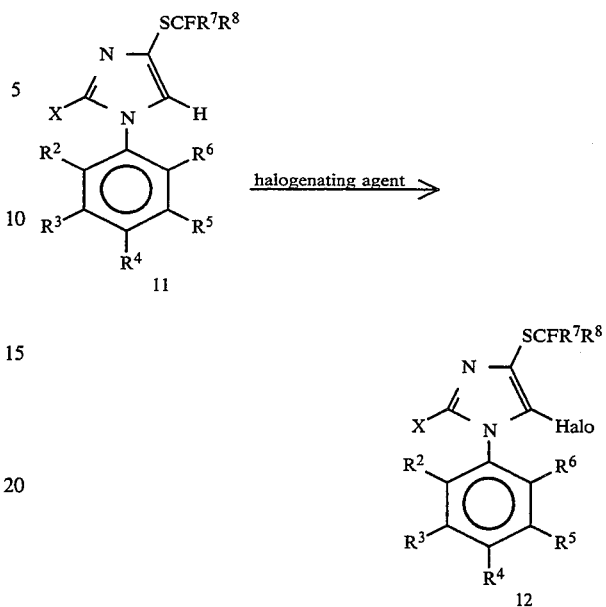

Thus a sulfide of the general formula 12, wherein Halo is a halogen atom, preferably Cl, Br or I and the other groups are as defined above, may be prepared by halogenating a sulfide intermediate of the general formula 11, with a halogenating agent, such as chlorine or bromine, N-chlorosuccinimide or N-bromosuccinimide. The reaction is conducted in an inert aprotic solvent, such as a chlorinated hydrocarbon, an ether, acetonitrile, or in a biphasic reaction medium which may be either a liquid-solid or a liquid-liquid system. When the biphasic reaction medium is a liquid-solid system, the liquid phase may be an aliphatic or aromatic hydrocarbon which may be halogenated. Preferred organic solvents are chlorinated aromatic hydrocarbon such as chlorobenzene. The solid phase is an inorganic base such as an hydroxyde or carbonate or hydrogen carbonate of alkaline or earth-alkaline metal. Preferred bases are carbonate and hydrogen carbonates of alkaline metals such as sodium carbonate and sodium hydrogen carbonate. When the biphasic reaction medium is a liquid-liquid system, one of the liquid phase is an organic phase which is mainly an aliphatic or aromatic hydrocarbon which may be halogenated. Preferred organic solvents are chlorinated aromatic hydrocarbons such as chlorobenzene. The other liquid phase is an aqueous phase which contains a phase transfer catalyst such as an alkylammonium halide.. The reaction may be carried out between about −50° C. and 150° C., preferably between about −10° C. and 100° C., depending on the reactivity of the intermediate 11 and the reactivity of the halogenating agent used. Typical procedures are similar to those reported in A. R. Katritzky et at., "Comprehensive Heterocyclic Chemistry", 1984, Vol. 5, Part 4A, Ed. Pergamon Press, p. 398 and in references therein.

The compounds of the general formula III, in which n is 0 and the other groups are as defined above, are also useful intermediates in the preparation of compounds of the general formula III, in which n is 1 or 2 and the other groups are as defined above. Their general preparations and the corresponding procedures are described in U.S. Ser. No. 07/606,518 cited above.

EXAMPLES

The following examples are given to illustrate the invention and some modes of realisation. It is not intended to restrict the invention to these particular examples.

Example 1

316 g (10.5 moles) of polyoxymethylene were added progressively at 10° C. to 551 g (11.25 moles) of sodium cyanide in 2 l of water, followed by the progressive addition of 1563 g (8.85 moles) of benzenesulphonyl chloride. The reaction mixture was further stirred at 10° C. To the previous reaction mixture were added 8 l of methylene chloride; then were introduced at 10° C. 1561 g(7.5 moles) of N-formyl-2,6-dichloro-4-fluoro aniline and 485 g (1.64 moles) of tetrabutylammonium chloride. The solution was stirred at 10° C. during 20 min., then mixed with 975 ml (9.75 moles) of an aqueous solution of sodium hydroxyde at 30%. After stirring 1 hour at 10° C., 2 l water and 2 l methylene chloride were added. The organic layer was washed with water and concentrated. Crystallisation in the mixture cyclohexane/isopropanol (75/25) supplied 1702 g (89% yield) of N-cyanomethyl, N-formyl 2,6-dichloro-4-fluoroaniline.

This product was characterized by proton nuclear magnetic resonance spectrometry in dimethylsulfoxid: the aromatic protons were found to give two doublets at a chemical shift of 7.71 and 7.76 ppm, each corresponding to a different conformer, with a coupling constant of 8.5 Hz.

Example 2

Cyanomethyl acetate was prepared according to the method described in Synth. Commun. 2, 215 (1972). A mixture of 2.78 g (10 millimole) of tetrabutylammonium chloride and 1 g (10 millimole) of cyanomethyl acetate was dissolved in 10 ml of dichloromethane. To the reaction mixture were added 2 g (9.6 millimoles) of N-formyl-2,6 dichloro-4-fluoroaniline and 3 ml (12 millimoles) of a 4 mole/l sodium hydroxyde aqueous solution. After stirring for 1 hour at room temperature, N-cyanomethyl-N-formyl-2,6-dichloro-4-fluoroaniline was obtained.

Example 3

To a solution of 6.16 g (29.6 millimoles) of N-formyl-2,6-dichloro-4-fluoroaniline in 30 ml of dichloromethane were added at room temperature 30 ml of water, 1.66 g of tetrabutylammonium chloride (5.9 millimole), 1.5 g (37.5 millimole) of sodium hydroxyde and finally a solution of 2.1 ml (33.0 millimole) of chloroacetonitfile in 3 ml of dichloromethane. After stirring for 1 hour at room temperature, the organic layer was washed with water, dried, concentrated, and washed with 100 ml of hexane to afford 5.7 g (78%) of N-cyanomethyl-N-formyl-2,6-dichloro-4-fluoroaniline.

Example 4

To 1513 g (6.12 moles) of the end product of example 1, in 15 l ethanol, were added at room temperature 1822 g (18 moles) of triethylamine. 510 g (15 moles) of hydrogen sulfide (gas) were introduced in this solution in 2.5 hour at 30° C. A stream of inert gas was passed through the reaction mixture for 8 hours at room temperature. Then, the mixture was concentrated, cooled down to 0° C. and filtered. The solid was washed with cold (−30° C.) ethyl alcohol and dried to give 1640 g of 2-[N-formyl-N-(2,6-dichloro-4-fluoro)phenyl]thionoacetamid (93% yield).

This product was characterized by proton nuclear magnetic resonance spectrometry in dimethylsulfoxid: the aromatic protons were found to give two doublets at a chemical shift of 7.59 and 7.66 ppm, each corresponding to a different conformer, with a coupling constant of 8.5 Hz.

What is claimed is:

1. A compound which is N-cyanomethyl, N-formyl 2,6-dichloro-4-fluoroaniline or 2-[N-formyl-N-(2,6-dichloro-4-fluoro)phenyl] thionoacetamid.

* * * * *